United States Patent [19]

Pollack

[11] 4,301,797
[45] * Nov. 24, 1981

[54] BALLOON-TIPPED EXTRACORPOREAL CANNULA APPARATUS AND METHOD FOR INSERTION OF SAME

[76] Inventor: Charles N. Pollack, 12311 Windsor Dr., Carmel, Ind. 46032

[*] Notice: The portion of the term of this patent subsequent to Feb. 20, 1996, has been disclaimed.

[21] Appl. No.: 962,909

[22] Filed: Nov. 22, 1978

Related U.S. Application Data

[63] Continuation-in-part of Ser. No. 796,362, May 12, 1977, Pat. No. 4,140,119.

[51] Int. Cl.³ .............................................. A61M 5/00
[52] U.S. Cl. ................................. 128/214 R; 128/348
[58] Field of Search .................................. 128/348–351, 128/214 R, 214.4, 240–241, 246, 344, 325

[56] References Cited

U.S. PATENT DOCUMENTS

| | | | |
|---|---|---|---|
| 2,919,697 | 1/1960 | Kim | 128/349 B |
| 3,185,151 | 5/1965 | Czorny | 128/214.4 |
| 3,331,371 | 7/1967 | Rocchi et al. | 128/349 B |
| 3,392,722 | 7/1968 | Jorgensen | 128/350 R X |
| 3,395,710 | 8/1968 | Stratton | 128/350 R |
| 3,995,617 | 12/1976 | Watkins et al. | 128/348 X |
| 4,014,317 | 3/1977 | Bruno | 128/348 X |
| 4,129,129 | 12/1978 | Amrine | 128/348 |
| 4,140,119 | 2/1979 | Pollack | 128/348 X |

FOREIGN PATENT DOCUMENTS 465204  12/1975  U.S.S.R. ..................... 128/349 B

*Primary Examiner*—Dalton L. Truluck
*Attorney, Agent, or Firm*—Woodard, Weikart, Emhardt & Naughton

[57] ABSTRACT

A balloon-tipped extracorporeal cannula apparatus suitable for use in a cardiac cannulation technique including a first elongated and flexible tube having an open proximal end and a distal tip with at least a plurality of holes near the distal end, at least one inflatable balloon on the inside wall of the first tube adjacent to the holes, and a second flexible tube communicating with the balloon for readily inflating and deflating the balloon. When inflated, the balloon completely occludes the lumen of the first tube and extends at least to a point between the most distal portion and the most proximal portion of the holes near the distal end of the first tube thereby only partially obstructing the holes. In some applications, the inflated balloon may completely occlude the holes and occupy the entire intraluminal space in the distal end of the first tube to protect against the introduction of any entrapped air into the circulatory system upon initial insertion of the cannula. A method is further provided for inserting a balloon-tipped extracorporeal cannula during a cardiac cannulation technique comprising filling the lumen of the cannula with fluid, inflating the balloon on the inside wall of the cannula near the holes at its distal tip, inserting the distal end of the cannula into the circulatory system of the person through a prepared incision and deflating the balloon thereby allowing fluid to flow between the cannula and the circulatory system.

23 Claims, 11 Drawing Figures

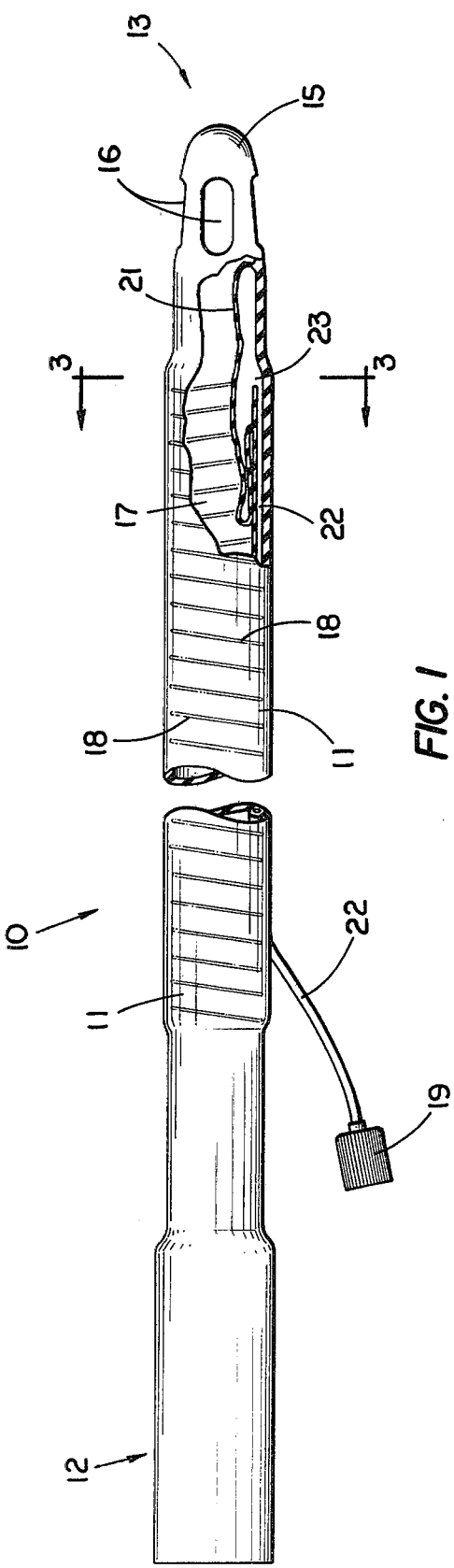
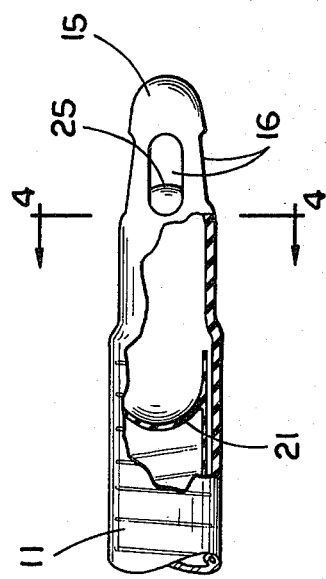
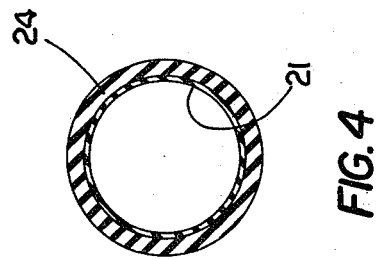
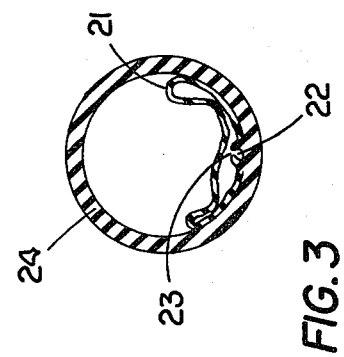

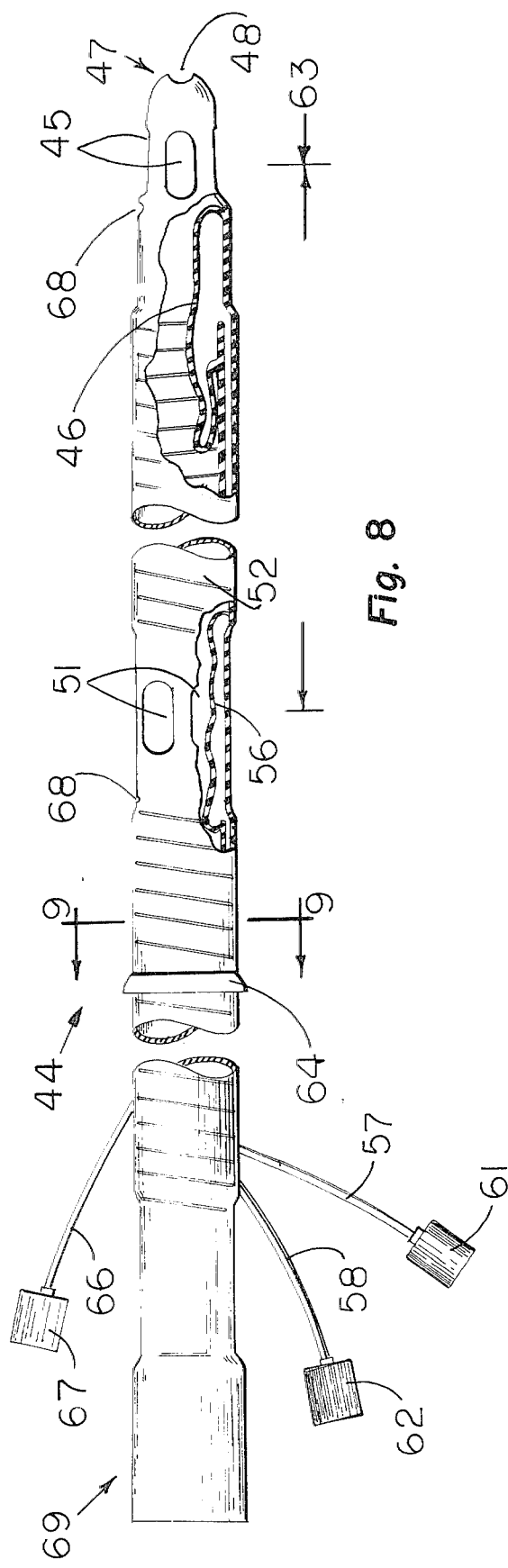
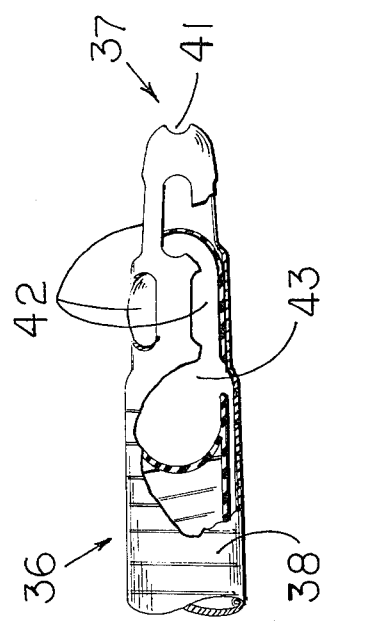
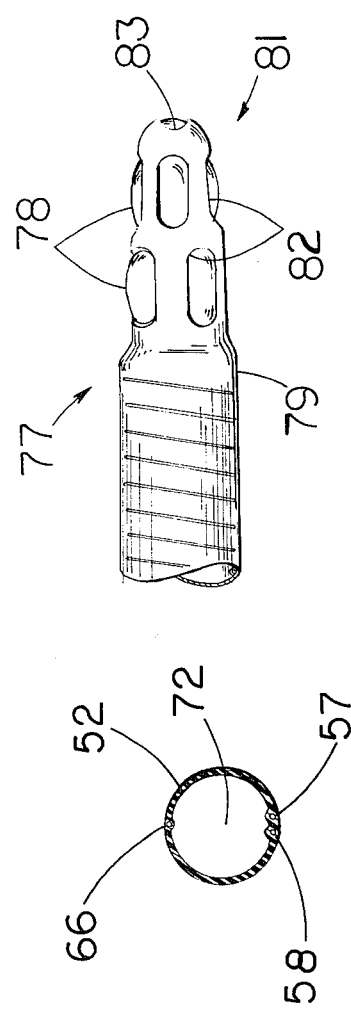
Fig. 8
Fig. 7
Fig. 11
Fig. 9

BALLOON-TIPPED EXTRACORPOREAL CANNULA APPARATUS AND METHOD FOR INSERTION OF SAME

BACKGROUND OF THE INVENTION

This application is a continuation-in-part application of my previously filed U.S. Patent application Ser. No. 796,362, filed May 12, 1977, now U.S. Pat. No. 4,140,119 and entitled "Balloon-Tipped Extracorporeal Cannula Apparatus and Method for Insertion of Same."

This invention relates to methods and apparata used in cannulation techniques, and particularly, to an improved cannula apparatus and method for its insertion suitable for use in a cardiac cannulation technique.

A cannula, or catheter as it may be called, is generally recognized as an elongated and flexible tube that may be inserted into a person's body in order to withdraw or inject various fluids. The prior art is replete with such cannulas and catheters, as well as with methods for their insertion and use.

The general use of inflatable ballons with such cannulas and catheters is also known in the art. In one instance, commonly referred to as a "bag" catheter, an externally attached balloon or "bag" is used to hold the catheter in place after insertion in order to allow prolonged or periodic withdrawal or injection of fluids into the body. A common use for such "bag" catheters, as disclosed in Rocchi et al., U.S. Pat. No. 3,331,371, is to insert the catheter by way of the urethra into a person's bladder in order to withdraw fluid from the bladder over a period of time. Another example of an externally attached inflatable balloon or collar used to stabilize the position of the cannula following insertion is found in Shinnick et al., U.S. Pat. No. 3,680,544, which discloses a transthoracic cannula-type device useful in cardiopulmonary resuscitation.

In other instances, inflatable balloons have been positioned inside the luminal cavity in the cannula or catheter in order to achieve a desired result. In Kim, U.S. Pat. No. 2,919,697, such an intraluminal inflatable balloon was used for the same purpose as above described, i.e., for anchoring the standard catheter drainage tube in the body after insertion. The above Rocchi reference, on the other hand, uses the intraluminal balloon or ball to completely cover the fluid holes in the catheter and thereby control the flow of fluid therethrough.

A rapidly-growing area of cannula technology concerns the technique of cardiac cannulation and the use of artificial heart-lung machine means to facilitate intricate and prolonged operations on the cardiac, pulmonary and circulatory systems. During such operations, cannulas which are connected to the artificial heart-lung machine means are first properly inserted through prepared incisions into the arterial and venous systems adjacent the heart, and even into the intracardiac chambers as well. Once properly positioned and in operation, the blood of the person is withdrawn or siphoned through the venous cannulas and pumped through the arterial cannulas back into the circulatory system by the artificial heart-lung machine means. The heart and lungs of the person can thereby be effectively bypassed, thus allowing the surgeon to operate on the heart.

A major problem encountered in all such cardiac cannulation techniques involves the introduction of air into the circulatory system during the insertion and positioning of the various venous, arterial and intracardiac cannulas. In this regard, the avoidance of any such introduction is extremely important because of the danger of stroke or other adverse effects such air may have on the circulatory system.

The present state of the art provides two possible methods for avoiding any such introduction of air during cardiac cannulation. One method involves first inserting the distal end of the cannula into the circulatory system while the tubing connecting the cannula to the heart-lung machine means is then vented by manipulating a drain line near the proximal end of the cannula thereby permitting the cannula to fill with the patient's blood. This method, however, does not prevent the possible introduction of air into the blood stream during initial insertion of the distal end of the cannula. In addition, it requires the extra steps of manipulating both the venting line and the external clamp, and cannot prevent the probable entrapment of air in the tube between this venting line and the clamp itself.

A second method of cannula insertion practiced in the present art involves first holding the cannula upright and filling it either with a serum or with blood through the plurality of holes near its closed distal tip. Then, the surgeon rapidly inserts the distal end of the cannula into the prepared incision in the circulatory system in order to avoid excessive spillage of the fluid, if at all possible. This method has its shortcomings both because of the mess created by the spilling fluid and because as the fluid empties, air may be again allowed into the cannula and later introduced into the circulatory system.

SUMMARY OF THE INVENTION

One embodiment of the present invention comprises a balloon-tipped extracorporeal cannula apparatus suitable for use in a cardiac cannulation technique including a first elongated and flexible tubular member having a proximal and a distal end, the proximal end being open, said first member including at least one first hole near the distal end thereof, a first inflatable balloon on the inside wall of the first member adjacent to the first hole therein, and means including a flexible tubular passageway communicating with the first balloon for readily inflating and deflating the first balloon. When inflated, this first balloon completely occludes the lumen of the first member and includes means for preventing the entrapment of any air near the distal end of the first member upon insertion of the distal end into the circulatory system of a person.

The above embodiment thus permits cannulation of the heart and adjacent vessels without the risk of trapping any air near the distal end of the cannulas and thereby eliminates any possibility of introducing this air into the circulatory system during the cannulation procedure.

One mode of practicing this above embodiment includes a first plurality of holes near this distal end, the means for preventing includes means for allowing liquid to wash freely across and through the unobstructed portion of the distal end of the first member after its insertion. This is accomplished by positioning the intralumenal balloon so that the most distal portion of the balloon, when inflated, extends to a point between the most distal portion and the most proximal portion of the holes nearest the distal end of the first member. This first balloon is further sufficiently large and extends along the inside wall of the first member a sufficient distance so that, when inflated, it completely occludes both the lumen of the first member and all more proximally positioned holes therein. This positioning eliminates both the need for manipulating any external venting line or tubing clamp and the mess and spillage of fluid characteristic of prior art methods. It further specifically prevents the entrapment of any air either distal of the holes in the distal tip of the first member or proximal of the holes between this first inflated balloon and the plurality of holes themselves, as would result with the use of catheters such as the ones disclosed in the Rocchi and Kim references.

This above positioning of the intraluminal balloon can also provide other advantages by only partially obstructing the holes near the distal end of the cannula, particularly where vessel or chamber obstruction is of major concern. For instance, the distal tip of the cannula may become wedged or stuck in a side vein or artery or in a confined area in an inner chamber of the heart during cannulation and thus threaten to occlude or block the vessel or chamber when such occlusion is both unexpected and not desirable. With the above mode, this result may be avoided because blood may still be able to wash or flow freely across and through the unobstructed portion of the distal end of the cannula after its insertion and before the balloon is deflated and the siphoning, or pumping, action begun. This provides a major advantage over such balloon catheters as disclosed in Rocchi, which completely obstruct the fluid holes in the catheter when the balloon is inflated thereby negating any possible bypass for the flow of blood if the cannula becomes unavoidably stuck.

In a second mode of practicing the above embodiment, this first member includes both a first plurality of holes including a hole in the distal tip thereof and a second plurality of holes spaced apart proximally from the first holes along this first member. A second inflatable balloon is then positioned on the inside wall of the first member adjacent the second holes therein. This second balloon, when inflated, completely occludes both the second holes and the lumen of the first member itself. The provision of the second holes permits the drainage or injection of blood from or into two areas adjacent the heart, e.g., when the tip of the cannula is placed in the inferior vena cava with the second more proximal holes positioned in the right atrium. A second example is when the tip of the cannula is positioned in the left ventricle whereas the second more proximal holes are positioned in the left atrium to allow drainage from both areas. In addition, a second flexible tubular passageway can be provided in the first member having an inlet opening near the proximal end thereof and an outlet opening near the distal end thereof, this second passageway being suitable for infusing any variety of solutions into the heart or the adjacent vessels upon insertion of the distal end into the circulatory system of a person during a cannulation procedure.

Still a third mode of practicing the above embodiment stresses the concern for preventing entrapped air from entering the circulatory system while minimizing any concern over vessel or cavity obstruction. In this third mode, the first balloon, when inflated, completely occludes both the first plurality of holes and the lumen of the first member while also preventing the entrapment of air in the distal tip. This can be accomplished in two ways. First, if the first member is without a hole in the distal tip, the first balloon must expand, or inflate, a sufficient amount to fully occupy this most distal intraluminal space while displacing any potentially entrapped air. If the first member does include a hole in the distal tip thereof, however, this first balloon must expand a sufficient amount to fully occupy the most distal intraluminal space and protrude from the distal tip hole thereby again preventing the introduction of any entrapped air into the circulatory system. This mode is useful in cannulating larger cavities in the heart, such as the left ventricle, which are without restrictive vessels draining in or out of the area thereby decreasing the concern over trauma caused by possible obstruction.

A second embodiment of the present invention comprises the method for inserting a cannula during a cardiac cannulation technique comprising filling the lumen of the cannula apparatus of the above embodiments with liquid, occluding the filled lumen by inflating the balloon(s) adjacent the hole(s) therein, inserting the distal end of the filled and occluded cannula into the circulatory system of a person through a prepared incision and then unoccluding the lumen of the cannula by deflating the balloon(s) thereby allowing liquid to flow between the cannula and the circulatory system.

One object of the present invention is therefore to provide a balloon-tipped extracorporeal cannula and method for its insertion that prevent the introduction of any trapped air into the circulatory system of the patient during cannulation.

Another object of the present invention is to provide a method for inserting a cannula during a cardiac cannulation which avoids the mess of liquid spillage and eliminate the need for external clamps or for venting trapped air in the cannula while preventing the possible introduction of such trapped air into the circulatory system.

Related objects and advantages of the present invention will be apparent from the following description.

BRIEF DESCRIPTION OF THE DRAWINGS

FIG. 1 is a fragmented side elevation of the balloon-tipped extracorporeal cannula comprising a perferred embodiment of the present invention with a portion broken away to reveal the partially collapsed balloon.

FIG. 2 is a partial side elevational of the cannula in FIG. 1 with a portion broken away to reveal the balloon when inflated.

FIG. 3 is a cross-sectional view of the cannula in FIG. 1 taken along line 3—3.

FIG. 4 is a cross-sectional view of the cannula in FIG. 2 taken along line 4—4.

FIG. 7 is a partial side elevation of a modified cannula apparatus in accordance with one embodiment of the present invention, with a portion broken away to reveal the first balloon when inflated.

FIG. 8 is a fragmented side elevation of a second modified cannula apparatus in accordance with one embodiment of the present invention, with a portion broken away to reveal the partially collapsed first and second balloons.

FIG. 9 is a cross-sectional view of the cannula in FIG. 8 taken along line 9—9.

FIG. 11 is a partial side elevation of a third modified cannula apparatus in accordance with one embodiment of the present invention.

DESCRIPTION OF THE PREFERRED EMBODIMENTS

Figure 5:
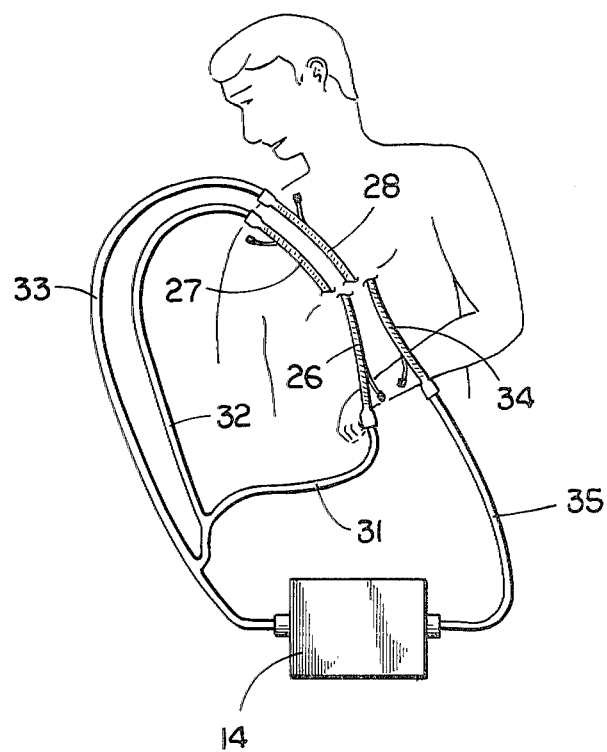
FIG. 5 is a reduced representation of four balloon-tipped extracorporeal cannulas of the present invention, as shown in FIG. 1, in use during a cardiac cannulation.

For the purposes of promoting an understanding of the principles of the invention, reference will now be made to the embodiments illustrated in the drawings and specific language will be used to described the same. It will nevertheless be understood that no limitation of the scope of the invention is thereby intended, such alterations and further modifications in the illustrated devices, and such further applications of the principles of the invention as illustrated therein being contemplated as would normally occur to one skilled in the art to which the invention relates.

Referring now to FIG. 1, the balloon-tipped cannula 10 comprising a preferred embodiment of the present invention is therein depicted. Cannula 10 includes a first elongated and flexible tube 11 which has both a proximal end 12 and a distal end 13. The proximal end of cannula 10 is open to allow the cannula to be attached to various secondary tubing which then connects the cannula to the desired equipment, such as the heart-lung machine means 14 in FIG. 5. Distal end 13, on the other hand, has a closed and thickened distal tip 15 and includes a plurality of holes 16 near this distal tip which allow fluid to flow between the lumen 17 of cannula 10 and the circulatory system of the person.

As stated above, tube 11 of the preferred embodiment is made of a flexible material, such as rubber or polyvinyl. It may also include a spiraling wire 18 which is molded into the cannula wall 24. This wire 18 reinforces the central portion of cannula 10 thereby facilitating easy handling and preventing any possibility of the cannula collapsing or being pinched shut and thus closing off the flow of blood to or from the patient. Other ways of reinforcing the tubular body of a cannula are known in the art and will adapt equally well to the present invention. In addition, no reinforcement may be needed if the tube material is sufficiently strong.

The dimensions of tube 11 may vary greatly according to the person's age and size, the number of cannulas used in the cannulation technique and the specific manufacturer of the cannulas used. The external cross-sectional diameter of the tube 11 may thus vary from about 1 cm. to about 2 cm. at its widest point, tube 11 of the preferred embodiment being about 1.5 cm. in diameter.

A first inflatable balloon 21 is positioned on the inside wall of tube 11 adjacent to and proximal of the holes 16. A second elongated and flexible tube 22 is connected to inflatable balloon 21 through an orifice or opening 23 in the cannula wall 24. Tube 22 then connects the balloon 21 to a supply of fluid (not shown) which is used to inflate and deflate the balloon during use of the cannula 10. Air may be used as a satisfactory inflating substance, however, it is desirable to use a liquid such as a saline solution because of the possible danger of a leak developing in the balloon which then could introduce air into the circulatory system of the person.

Although various fluid supplies and means of inflating and deflating balloon 21 may be used in conjunction with the present invention, in the preferred embodiment tube 22 connects to a female attachment or adapter 19 which receives a nipple tip syringe (not shown). This syringe is used to inject or withdraw fluid through tube 22 thereby inflating and deflating the balloon.

In constructing a balloon-tipped extracorporeal cannula pursuant to this embodiment, inflating tube or passageway 22 may extend completely along the inside or outside of the cannula tube 11. However, cannula 10 of the preferred embodiment incorporates the inflating tube or lumen 22 into the cannula wall 24 through the major portion of tube 11, as better shown in FIG. 3. Tube 22 of the preferred embodiment is thereby also protected by reinforcing wire 18 before it finally exits the cannula wall near the proximal end 12 of tube 11.

When deflated, collapsible balloon 21 lies flush against the inside wall of tube 11 thereby allowing fluid to flow freely through cannula 10 with a minimal amount of turbulence. The caliber or size of the deflated balloon 21 as it lies against the wall is such that it provides no appreciable blockage of the lumen cavity 17 or the fluid passing therethrough. In FIGS. 1 and 3, balloon 21 is shown not completely deflated for the convenience and understanding of the reader and thus obstructs the lumen 17 substantially more than when fully deflated.

Figure 6:
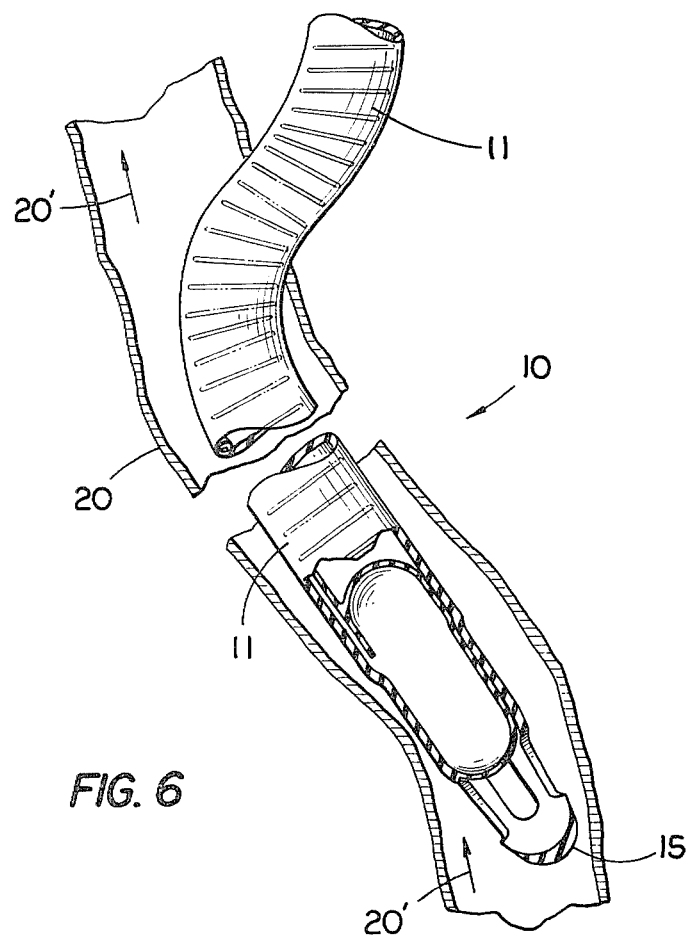
FIG. 6 is a part-sectional view of the distal end of the cannula in FIG. 2 positioned in the inferior vena cava adjacent a person's heart during a cardiac cannulation.

When inflated, as shown in FIGS. 2, 4, and 6, balloon 21 completely occludes the lumen 17 of cannula 10. The most distal portion 25 of the balloon 21 also extends to a point between the most distal portion and most proximal portion of the holes 16 near the distal end of tube 11. FIG. 4 depicts a cross-sectional view of cannula 10 in FIG. 2 taken at the most proximal portion of the holes 16. As it reveals, the inflated balloon completely occludes the cannula lumen at that point thereby preventing the flow of any fluid through the cannula. More importantly, by occluding the lumen 17 right up to the holes 16, the inflated balloon also prevents the entrapment of any air in the tube 11 proximal of holes 16 and thereby avoids the possible introduction of any such entrapped air into the circulatory system upon insertion of the cannula.

As previously discussed, an additional feature of the balloon-tipped extracorporeal cannula of the preferred embodiment is that the inflated balloon only partially obstructs the holes 16 near the distal end 13 of the cannula. Therefore, no air can be trapped in the closed distal tip during insertion, and the person's blood may be able to wash or flow across and through the unobstructed portion of the distal end of tube 11 if it becomes wedged or stuck in a vessel or chamber after its insertion and prior to deflation of the balloon 21. This minimizes the possibility of interference with normal blood flow prior to initiating the artificial heart-lung action and thus provides less chance of vessel obstruction impairing the flow of blood through the circulatory system. FIG. 6 depicts a venous cannula 10 of the present invention positioned in an inferior vena cava 20 during a cardiac cannulation and prior to deflation of the balloon. The blood is flowing in the direction of arrow 20'.

A second embodiment of the present invention comprises a method of inserting balloon-tipped extracorporeal cannula 10 into a person's circulatory system during a cardiac cannulation technique. The first step in this method involves filling the lumen 17 of the cannula 10 with a fluid. For this purpose, the fluid may be either blood or a compatible electrolytic solution such as a saline solution and the filling may be accomplished through either the proximal or distal end of the cannula. In the preferred embodiment, the cannula 10 is filled with a saline solution through the holes 16 near the closed distal tip.

The next step is occluding the lumen 17 near the holes 16 at its closed distal tip 15 by inflating balloon 21. The distal end of the filled and occluded cannula 10 is then inserted into the circulatory system of the person through a prepared incision. And lastly, the lumen 17 is unoccluded by deflating balloon 21 thereby allowing fluid to flow between the cannula and the circulatory system of the person.

FIG. 5 depicts the preferred method and balloon-tipped extracorporeal cannula 10 of the present invention in use during a cardiac cannulation. Venous cannulas 26 and 27, constructed according to the present invention, are first positioned in the superior and inferior vena cava, respectively. An intracardial cannula 28 is also positioned inside the left ventricle of the heart in order to decompress the heart and keep the volume of blood in it minimal thereby preventing any possibility of the heart distending during the operation. These cannulas are in turn connected through tubing 31, 32 and 33, respectively, to the input side of a heart-lung machine means 14. An arterial cannula return line 34 is then positioned in the aorta or femoral artery in order to recirculate the blood from the heart-lung machine means 14 through tubing 35 and back into the circulatory system of the person.

In practice, both the number and location of the cannulas used in a cardiac cannulation technique can vary according to a variety of factors, such as the specific type of operation involved. In the preferred embodiments, four cannulas are used in order to assure proper and complete cannulation. The cannulas are first properly inserted into the circulatory system according to the above-described method. Then, when all four are properly positioned, the balloons are deflated and the siphoning and recirculating action through the heart-lung machine means 14 is begun. At this time, the surgeon can operate on the person's heart, lungs or adjacent vessels while the machine 14 artificially maintains the heart and lung functions. When the operation is completed, the cannulas are again occluded by inflating the intraluminal balloons or clamping them thus allowing the person's heart and lungs to resume their normal functions.

Turning now to FIG. 7, a partial view of a modified cannula 36 in accordance with the present invention is therein depicted. Specifically, cannula 36 is substantially similar to cannula 10 of the preferred embodiment as described above, with but a few modifications. First, the distal end 37 of flexible tubular member 38 includes a hole 41 in the distal tip thereof.

Second, cannula 36 includes additional holes 42 near the distal end 37 of the cannula. First balloon 43 is constructed and positioned similar to preferred cannula 10 and, upon inflation, extends to a point between the most distal portion and the most proximal portion of the holes 42 nearest the distal tip to thereby prevent the entrapment of any air in the distal end of the cannula during insertion into the circulatory system of a person. First balloon 43, when inflated, also completely occludes the lumen of first member 38 and further blocks, or occludes, the more proximal holes 42 near distal end 37. In this way, no air can be trapped in the distal end 37 during insertion of the cannula.

In addition, once inserted and first balloon 43 is deflated, these additional holes permit the blood to flow more freely through the distal end of the cannula during operation of the heart-lung machine means means (not shown). Still another advantage of this modified cannula 36 is that after insertion and prior to deflation of the first balloon 43, the hole 41 in the distal tip permits the freer flow of the person's blood across and through the unobstructed portion of the distal end of first member 38. This further minimizes the possibility of interference with normal blood flow prior to intiating the artificial heart-lung action and provides less chance of vessel obstruction or tissue buildup in the cannula tip which might impair, or block, the flow of blood through the circulatory system.

FIG. 8 depicts a further modification of a cannula apparatus in accordance with the present embodiments. Specifically, cannula 44 includes a plurality of holes 45 and a first inflatable balloon 46 similar in all respects to the holes 16 and balloon 21 of preferred cannula 10. The distal end 47 of cannula 44 also includes a hole 48 in the distal tip thereof to further enhance the free wash, or flow, of liquid through the unobstructed portion of distal end 47 when inserted in the circulatory system.

Figure 10:
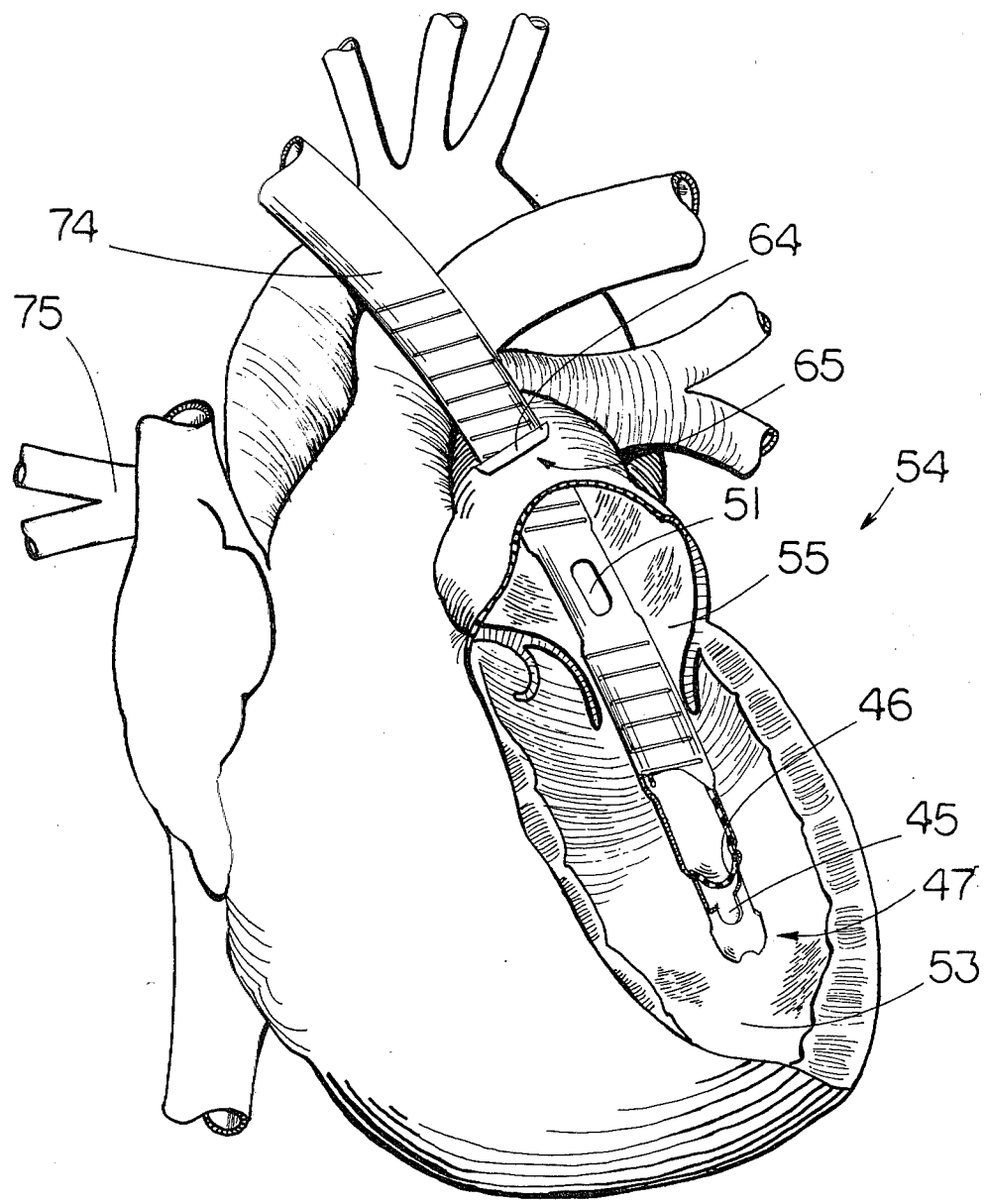
FIG. 10 is a representation of a cannula similar to the one in FIG. 8 in use during a cardiac cannulation, with the first holes positioned in the left ventricle of the heart and the second proximal holes positioned to drain blood from the left atrium.

The major modification in cannula 44, however, is the addition of a second plurality of holes 51 spaced apart axially along first member 52 from the first holes 45 adjacent to distal end 47. The purpose for the second set of holes is to permit the simultaneous drainage of blood from two separate areas during a cardiac cannulation procedure. For example, FIG. 10 depicts a simplified representation of an exposed heart 54 during cardiac cannulation using a cannula 74, similar to cannula 44 in FIG. 8. Distal end 47 has been surgically positioned in the left ventricle area 53 of the heart 54 for drainage purposes. Second holes 51, also by way of the surgical incision, are positioned in the left atrium area 55. Blood can therefore be simultaneously drained from both the left atrium and left ventricle areas during cannulation with the use of but a single cannula, or catheter, 74. A second example of the use of a cannula such as cannula 44 would be the positioning of the distal end and first holes in the inferior vena cava adjacent the heart with the second more proximal holes surgically located to simultaneously drain blood from the right atrium area during cannulation.

Referring back to FIG. 8, a second inflatable balloon 56 is also attached to the inside wall of first member 52 adjacent to second holes 51. This second balloon 56, when inflated, completely occludes the lumen of first member 52 while also completely blocking, or occluding, the second holes 51. In this way, when inflated, second balloon 56 prevents the loss or entrance of any fluid, such as air or solution, through second holes 51 while also preventing the entrapment of any air in these second holes that could be subsequently released in the circulatory system.

The inflation and deflation of first and second balloons 46 and 56 in cannula 44 can be accomplished by either independent or dependent means. For example, a single flexible tube or passageway either attached to or incorporated in the wall of first member 52 could be arranged to communicate with both balloons for their simultaneous inflation and deflation by means of a single female attachment or adaptor and a single standard syringe as discussed above in connection with the preferred cannula 10.

However, in cannula 44, both a first and a second flexible tubular passageway 57 and 58, as better shown in FIG. 9, are provided in the wall of first member 52 for independent inflation and deflation of the two balloons. Two female attachments or adaptors 61 and 62 are then provided which can receive any nipple tip syringe (not shown) for injection or withdrawal of fluid through the tubes thereby inflating or deflating the balloons. By providing this independent control, it is possible, as shown in FIG. 10 to inflate first balloon 46 of cannula 74 while maintaining second balloon 56 in its collapsed position. In this way, drainage of blood would stop from the left ventricle area whereas blood would continue to drain from the more proximal left atrium area.

Although not possible with modified cannula 44, it is further contemplated that cannula apparata can be developed in which two separate lumens are provided in a single first flexible tubular member, as by dividing the single lumen with a flexible film or wall. By so doing, and with the provision of two independent balloons and sets of holes similar to cannula 44, it would be further possible to occlude or block the proximal holes while maintaining the more distal balloon in its collapsed condition. In this way, and analogizing to FIG. 10, blood could be continually drained from the left ventricle area while no blood is drained from the left atrium area during cardiac cannulation. Such modifications are clearly within the contemplation and scope of the disclosure herein and the claims attached hereto.

The distance separating the first and second holes 45 and 51, respectively, can vary substantially according to design and other considerations. As represented by numeral 63 in FIG. 8, this distance is entirely dependent upon the two areas selected for drainage and the distance through the prepared incision separating these areas. Other factors, such as the age of the person and the relative size of the heart must, of course, be taken into consideration in arriving at this required distance. Generally, distance 63 will vary between about 5 cm. and about 15 cm.

Cannula 44 includes two further improvements of importance to cardiac cannulation procedures. First, cannula 44 includes an enlarged circular marker 64 fixedly attached to the outer surface of first member 52 proximal of the second holes 51. These markers are precisely positioned along the tubular first members of cannulas in accordance with the present invention and are useful as indicators to the surgeon as to the position of the cannula during the insertion procedure.

Using FIG. 10 as an example, the surgeon has first determined the distance 63 required to properly position the first and second holes 45 and 51 in the left ventricle and left atrium areas 53 and 55, respectively. He has determined the point of initial entry into the circulatory system, generally indicated by arrow 65, and knows the distance the cannula must be inserted through the prepared incision for proper positioning. By attaching marker 64 at this required distance, e.g., as by sliding the marker along the outer surface of first member 52 or by some other commonly practiced technique, the surgeon can insert the cannula through the prepared incision until he feels, or sees, this marker reach its proper position as depicted in FIG. 10. The surgeon is then assured the cannula is properly positioned, and he can proceed to the next step in the cannulation procedure.

It should be noted that FIG. 10 depicts a pulmonary cannulation wherein entry was achieved through an incision in the upper left atrium area of the heart. Another accepted surgical procedure for cannulating these left atrium and left ventricle regions calls for entry through an incision in a pulmonary vein 75 which drains into a remote region in the left atrium not shown in FIG. 10.

The second additional feature incorporated into cannula 44 is a means including a third flexible tube or passageway 66 for infusing a solution into the cannulated heart of a person upon insertion and proper positioning of the cannula apparatus. In cannula 44, this means is accomplished by incorporating a third passageway 66 into the wall of first member 52. This third passageway includes an inlet end equipped with an appropriate female adapter or attachment 67 and at least one outlet opening or discharge 68 adjacent to both the first and second holes 45 and 51, although additional discharge openings are desirable.

This infusion tube, as it is commonly called, is beneficial because it permits the ready infusion of blood or other solutions for a variety of purposes. For example, it is often desirable to infuse blood or some variety of cooling crystalloid solution into the left ventricle or other area in the heart to provide additional cooling for myocardial protection. Multiple discharge openings, or orifices, located circumferentially around the cannula are often desirable because they permit the cooling fluid to be ejected evenly throughout the cannulated area to thereby cool the myocardial wall in preparation for further surgical procedure. Regardless, however, the injected fluid is then siphoned back to the heart-lung machine means via the multiple cannulation holes 45 and 51 positioned in the cannulated areas.

The method of using cannula 44 is as follows: After connecting the open proximal end 69 of the cannula to a suitable heart-lung machine means (not shown), the lumen 72 is then filled with blood or a compatible electrolytic solution, this initial filling being to the second more proximal holes 51. The second balloon 56 is then inflated be means of passageway 57 and attachment 61 to completely occlude the lumen of cannula 44 at that point and obstruct the second holes 51 thereby preventing the entrapment of any air at this location.

The filling of lumen 72 distally from second balloon 56 then proceeds to first holes 45. At this point, first balloon 46 is inflated also completely occluding the lumen to a point between the most distal portion and the most proximal portion of the first holes 45 thereby preventing the entrapment of any air in the distal end 47 of the cannula.

With the cannula completely filled and occluded, the distal end 47 is then inserted into the circulatory system of the person through a prepared incision. Either with or without the aid of a marker, or ridge, 64, the inserted cannula is properly positioned in the circulatory system with the first and second holes located in the proposed drainage areas, e.g., as shown in FIG. 10.

Lastly, if cannulation and drainage of both areas are desired, both the first and second balloons 46 and 56 are deflated and the dual cannulation is begun. As described above, however, it is possible to deflate only second balloon 56 permitting drainage only of the upper cardiac area until such time that drainage of the lower area is also desired.

FIG. 11 depicts a cannula apparatus 77 comprising a further modification of the preferred embodiment described above. Specifically, the balloon 78 is so attached to the intraluminal wall 79 and so proportioned that when inflated, it expands to completely fill and occlude the intraluminal space in the distal end 81 of the cannula. The inflated balloon thus obstructs all distally positioned holes 82 including the hole 83 located in the distal tip. In this way, the inflated balloon 78 prevents the entrapment of any air in the distal end of the cannula prior to its insertion and therefore protects against the introduction of such air into the circulatory system during pulmonary cannulation.

This feature of total obstruction of the distal holes 82 and 83 in the cannula is seen to be advantageous when concern over vessel or cavity obstruction is minimal in relation to the concern to avoid air entrapment during initial insertion. For example, this situation occurs when, as depicted in FIG. 10, drainage is to be performed within a relatively large cavity such as the left ventricle which has no major vessels either draining into or exiting the cavity to warrant concern about their possible obstruction. Under such circumstances, there is little need for free flow, or wash, of blood across and through the unobstructed portion of the distal end of the cannula, in contrast to the circumstance depicted in FIG. 6. The concern to avoid the introduction of entrapped air into the circulatory system is of first priority, and a cannula constructed as shown in FIG. 11 can be readily used to guard against this happening.

As shown by the above disclosure, the method and balloon-tipped cannulas of the present invention permit cannulation of the heart and vessels without the risk of introducing trapped air into the circulatory system, as commonly experienced in the prior art. The present invention also eliminates the need for external cannula manipulation, such as the venting of trapped air, or the use of clamps to block the secondary tubing while the cannula fills with fluid.

It should also be noted that although the above embodiments have disclosed first and second pluralities of holes in the first tubular members, it is possible and even desirable under certain circumstances to employ only one hole in the cannula body. For example, one hole is ample to achieve proper infusion of blood back into the circulatory system through properly positioned arterial cannulas. Therefore, the use of only one hole in place of either the first or second pluralities, or both, disclosed above is clearly within the scope and contemplation of the present invention as disclosed and claimed herein.

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected.

I claim:

1. A balloon-tipped extracorporeal cannula apparatus suitable for use in a cardiac cannulation technique comprising:
   (a) a first elongated and flexible tubular member having a proximal and a distal end, the proximal end being open, said first member including at least one first hole near the distal end thereof;
   (b) a first inflatable balloon on the inside wall of said first member adjacent to the first hole therein, said first balloon, when inflated, completely occluding the lumen of said first member and including means for preventing the entrapment of any air near the distal end of said first member upon insertion of the distal end into the circulatory system of a person; and
   (c) means, including a flexible tubular passageway communicating with said first balloon, for readily inflating and deflating said first balloon, said first member includes a hole in the distal tip thereof.

2. The apparatus of claim 1 wherein said first member includes a first plurality of holes near the distal end thereof.

3. A balloon-tipped extracorporeal cannula apparatus suitable for use in a cardiac cannulation technique comprising:
   (a) a first elongated and flexible tubular member having a proximal and a distal end, the proximal end being open, said first member including at least one first hole near the distal end thereof;
   (b) a first inflatable balloon on the inside wall of said first member adjacent to the first hole therein, said first balloon, when inflated, completely occluding the lumen of said first member and including means for preventing the entrapment of any air near the distal end of said first member upon insertion of the distal end into the circulatory system of a person; and
   (c) means, including a flexible tubular passageway communicating with said first balloon, for readily inflating and deflating said first balloon, said first member includes a first plurality of holes near the distal end thereof, said means for preventing is that said first balloon, when inflated, completely occludes said first holes and occupies the entire intraluminal space in the distal end of said first member to the exclusion of any entrapped air.

4. A balloon-tipped extracorporeal cannula apparatus suitable for use in a cardiac cannulation technique comprising:
   (a) a first elongated and flexible tubular member having a proximal and a distal end, the proximal end being open, said first member including at least one first hole near the distal end thereof;
   (b) a first inflatable balloon on the inside wall of said first member adjacent to the first hole therein, said first balloon, when inflated, completely occluding the lumen of said first member and including means for preventing the entrapment of any air near the distal end of said first member upon insertion of the distal end into the circulatory system of a person;
   (c) means, including a flexible tubular passageway communicating with said first balloon, for readily inflating and deflating said first balloon; and
   (d) means, including a flexible tubular passageway in said first member having an inlet opening near the proximal end thereof and an outlet opening near the distal end thereof, for infusing a solution upon insertion of the distal end of said first member into the circulatory system of a person during cannulation.

5. A balloon-tipped extracorporeal cannula apparatus suitable for use in a cardiac cannulation technique comprising:
   (a) a first elongated and flexible tubular member having a proximal and a distal end, the proximal end being open, said first member including at least one first hole near the distal end thereof;
   (b) a first inflatable balloon on the inside wall of said first member adjacent to the first hole therein, said first balloon, when inflated, completely occluding the lumen of said first member and including means for preventing the entrapment of any air near the distal end of said first member upon insertion of the distal end into the circulatory system of a person; and (c) means, including a flexible tubular passageway communicating with said first balloon, for readily inflating and deflating said first balloon, said first member includes a first plurality of holes near the distal end thereof, said means for preventing includes means for allowing liquid to wash freely across and through the unobstructed portion of the distal end of said first member upon insertion of the distal end into the circulatory system of a person.

6. The apparatus of claim 5 wherein the means for preventing and for allowing is that the most distal portion of said first balloon, when inflated, extends to a point between the most distal portion and the most proximal portion of the holes near the distal end of said first member.

7. The apparatus of claims 3, 4 or 5 wherein said first member includes a hole in the distal tip thereof.

8. A balloon-tipped extracorporeal cannula apparatus suitable for use in a cardiac cannulation technique comprising:

(a) a first elongated and flexible tubular member having a proximal and a distal end, the proximal end being open, said first member including at least one first hole near the distal end thereof, said first member further including at least one second hole therein spaced apart axially from the first hole;

(b) a first inflatable balloon on the inside wall of said first member adjacent to the first hole therein, said first balloon, when inflated, completely occluding the lumen of said first member and including means for preventing the entrapment of any air near the distal end of said first member upon insertion of the distal end into the circulatory system of a person;

(c) means, including a flexible tubular passageway communicating with said first balloon, for readily inflating and deflating said first balloon;

(d) a second inflatable balloon on the inside wall of said first member adjacent to the second hole therein, said second balloon, when inflated, completely occluding the second hole and lumen of said first member and preventing the entrapment of any air therein; and (e) means including a second flexible tubular passageway communicating with said second balloon for readily inflating and deflating said second balloon independently of said first balloon.

9. A balloon-tipped extracorporeal cannula apparatus suitable for use in a cardiac cannulation technique comprising:

(a) a first elongated and flexible tubular member having a proximal and a distal end, the proximal end being open, said first member including a first plurality of holes near the distal end thereof, said first member further including at least one second hole therein spaced apart axially from the first holes;

(b) a first inflatable balloon on the inside wall of said first member adjacent to the first hole therein, said first balloon, when inflated, completely occluding the lumen of said first member and including means for preventing the entrapment of any air near the distal end of said first member upon insertion of the distal end into the circulatory system of a person, said means for preventing further including means for allowing liquid to wash freely across and through the unobstructed portion of the distal end of said first member upon insertion of the distal end into the circulatory system of a person;

(c) means, including a flexible tubular passageway communicating with said first balloon, for readily inflating and deflating said first balloon;

(d) a second inflatable balloon on the inside wall of said first member adjacent to the second hole therein, said second balloon, when inflated, completely occluding the second hole and lumen of said first member and preventing the entrapment of any air therein; and (e) means including a second flexible tubular passageway communicating with said second balloon for readily inflating and deflating said second balloon independently of said first balloon.

10. The apparatus of claim 9 wherein said first member includes a second plurality of holes therein spaced apart axially from the first holes.

11. The apparatus of claim 10 wherein the first and the second holes are spaced apart along said first member a distance of between about 5 cm. and about 15 cm.

12. The apparatus of claim 11 wherein the distance separating the first and the second holes is sufficient to allow positioning of the distal end of said first member and the first holes therein in the inferior vena cava of a human heart while the second holes are positioned in the right atrium of the heart during cardiac cannulation.

13. The apparatus of claim 10 wherein the distance separating the first and the second holes is sufficient to allow positioning of the distal end of said first member and the first holes therein in the left ventricle of a human heart while the second holes are positioned in the left atrium of the heart during cardiac cannulation.

14. The apparatus of claim 13 additionally comprising means, including a third flexible tubular passageway in said first member having an inlet opening near the proximal end thereof and an outlet opening near the first and the second holes in said first member, for infusing a solution into the circulatory system of a person during cannulation.

15. The apparatus of claim 14 wherein the means for preventing and for allowing is that the most distal portion of said first balloon, when inflated, extends to a point between the most distal portion and the most proximal portion of the first holes near the distal end of said first member.

16. The combination comprising:
(a) a heart-lung machine means; and
(b) the cannula apparatus of claim 15 connected to said machine means.

17. The combination comprising:
(a) a heart-lung machine means;
(b) a balloon-tipped extracorporeal cannula apparatus suitable for use in a cardiac cannulation technique connected to said machine means, said cannula apparatus comprising:
 (1) a first elongated and flexible tubular member having a proximal and a distal end, the proximal end being open, said first member including at least one first hole near the distal end thereof;
 (2) a first inflatable balloon on the inside wall of said first member adjacent to the first hole therein, said first balloon, when inflated, completely occluding the lumen of said first member and including means for preventing the entrapment of any air near the distal end of said first member upon insertion of the distal end into the circulatory system of a person; and (3) means, including a flexible tubular passageway communicating with said first balloon, for readily inflating and deflating said first balloon.

18. A method for inserting a cannula during a cardiac cannulation technique comprising:
   (a) filling the lumen of a cannula with liquid, the cannula including a first elongated flexible tubular member defining the lumen therein and having a proximal and a distal end, the proximal end being open, said first member including at least one first hole near the distal end thereof and at least one second hole spaced apart proximally therefrom, said filling comprising filling the lumen to the second hole in the first member;
   (b) occluding the partially filled lumen of the cannula near the second hole, said occluding comprising inflating a second balloon on the inside wall of the first member adjacent to the second hole therein;
   (c) filling the remaining portion of the lumen distally from the second inflated balloon;
   (d) occluding the filled lumen of the cannula near the first hole at the distal end thereof, said occluding comprising inflating a first balloon on the inside wall of the first member adjacent to and proximal of the first hole therein, said occluding further being as to prevent the entrapment of any air near the distal end of the first member upon insertion thereof into the circulatory system of a person;
   (e) inserting the filled and occluded cannula into the circulatory system of a person through a prepared incision, said inserting including positioning the first and the second hole in the areas to be cannulated; and
   (f) unoccluding the second hole in the cannula thereby allowing liquid to flow between the cannula and the circulatory system through the second hole, said unoccluding comprising deflating the second balloon on the inside wall of the cannula.

19. The method of claim 18 wherein said first member includes a first plurality of holes near the distal end thereof and a second plurality of holes spaced proximally therefrom.

20. The method of claim 19 wherein said occluding comprises completely occluding the first holes and occupying the entire intraluminal space in the distal end of the first member to the exclusion of any entrapped air.

21. The method of claim 19 wherein said occluding further comprises allowing liquid to wash freely across and through the unobstructed portion of the distal end upon insertion thereof into the circulatory system of a person.

22. The method of claim 21 wherein said unoccluding further comprises deflating the first balloon on the inside wall of the cannula thereby allowing liquid to flow between the cannula and the circulatory system through both the first and the second holes in the first member.

23. The method of claim 22 additionally comprising infusing a solution into the cannulated areas in the circulatory system of the person during the cannulation procedure.

* * * * *